(12) United States Patent
Harder et al.

(10) Patent No.: US 12,233,171 B2
(45) Date of Patent: Feb. 25, 2025

(54) CONTAINER, CLOSURE LID, AND VESSEL FOR TRANSPLANT OBJECTS, AND METHODS AND SYSTEMS FOR PROVIDING THREE-DIMENSIONAL STRUCTURE DATA AND FOR STERILIZING A TRANSPLANT OBJECT

(71) Applicant: CORLIFE OHG, Hannover (DE)

(72) Inventors: Michael Harder, Hildesheim (DE); Marco Lux, Hannover (DE)

(73) Assignee: Corlife OHG, Hannover (DE)

( * ) Notice: Subject to any disclaimer, the term of this patent is extended or adjusted under 35 U.S.C. 154(b) by 410 days.

(21) Appl. No.: 17/786,825

(22) PCT Filed: Dec. 11, 2020

(86) PCT No.: PCT/EP2020/085670
§ 371 (c)(1),
(2) Date: Jun. 17, 2022

(87) PCT Pub. No.: WO2021/122346
PCT Pub. Date: Jun. 24, 2021

(65) Prior Publication Data
US 2023/0025854 A1 Jan. 26, 2023

(30) Foreign Application Priority Data
Dec. 20, 2019 (DE) ...................... 10 2019 135 506.0

(51) Int. Cl.
*A61L 2/00* (2006.01)
*A01N 1/02* (2006.01)

(52) U.S. Cl.
CPC .......... *A61L 2/0029* (2013.01); *A01N 1/0263* (2013.01); *A61L 2202/122* (2013.01); *A61L 2202/182* (2013.01)

(58) Field of Classification Search
CPC ................ A01N 1/0263; A61L 2/0029; A61L 2202/122; A61L 2022/182
See application file for complete search history.

(56) References Cited

U.S. PATENT DOCUMENTS 6,046,046 A 4/2000 Hassanein

FOREIGN PATENT DOCUMENTS

| WO | 1996/039027 A1 | 12/1996 |
| WO | 1997/045527 A1 | 12/1997 |

(Continued)

*Primary Examiner* — Nicole M Ippolito
*Assistant Examiner* — Hanway Chang
(74) *Attorney, Agent, or Firm* — WCF IP

(57) ABSTRACT

The invention relates to a container (1) for holding a transplant object (2) and to a closure lid (4) and a vessel (3) for such a container (1). To facilitate an improved and reliable analysis and treatment of transplant objects (2), the intention being to implement particularly sparing handling, which is also protected against environmental influences, of the transplant object (2), it is proposed that the container (1) be transmissive for radiation that facilitates radiological imaging and/or a sterilization by means of ionizing radiation of the transplant object (2) held in the container (1) and that the closure lid (4) and/or the vessel (3) have one or more affixment structures (5) for fastening the transplant object (2) in the container (1). Moreover, a method and a system for providing three-dimensional structure data of a transplant object are proposed, by means of which the information obtained by the analysis is rendered better usable for medical staff. Moreover, a method and a system for sterilizing a transplant object (2) by means of ionizing radiation are described.

18 Claims, 4 Drawing Sheets

(56) References Cited

FOREIGN PATENT DOCUMENTS

| | | |
|---|---|---|
| WO | 1998/036992 A1 | 8/1998 |
| WO | 2009/123018 A1 | 10/2009 |

CONTAINER, CLOSURE LID, AND VESSEL FOR TRANSPLANT OBJECTS, AND METHODS AND SYSTEMS FOR PROVIDING THREE-DIMENSIONAL STRUCTURE DATA AND FOR STERILIZING A TRANSPLANT OBJECT

The invention relates to a container for receiving a transplant object, and to a closure lid and a vessel for such a container. The invention also relates to a method and a system for providing three-dimensional structure data of a transplant object. The invention moreover relates to a method and a system for sterilizing a transplant object by means of ionizing radiation.

In medicine, transplantation or organ transplantation denotes the transplantation of organic body parts or body tissues. It is in contrast to implantation, in the case of which artificial implants rather than organic material are placed inside a living being. Consequently, the transplant object is organic tissue; by way of example, this could be human or animal organs, or parts thereof. By way of example, such a transplant object could be a heart valve, which for instance as a donor valve can be brought into a human body. For improved handling and for improved acceptance by the receiver body, the heart valve may have been decellularized in particular, and may consequently be available in substantially cell-free fashion.

Storage, treatment and handling of the transplant object is implemented in surroundings that are as sterile as possible, for example in clean rooms, in order to be able to ensure the necessary low-germ or germ-free property of the transplant object. However, there inevitably are situations in which the transplant object needs to be transported, for example, and to this end temporarily leaves the sterile surroundings. In practice, transplant objects are predominantly transported in closed bags or containers in polystyrene or cooling boxes.

To identify a structurally suitable transplant object during the transplantation and in order to assess the quality of the transplant object, the objects are analyzed by trained staff and the determined properties such as for example the shape, size and morphological peculiarities are recorded in written records. On account of the subjective perception of the staff carrying out the analysis, this procedure for describing and verifying the suitability of the object for the envisaged transplantation is susceptible to errors and fraught with risk.

Additionally, it is possible to make and provide photographic or radiological recordings of the transplant object. However, for these recordings, the transplant object has to be taken from the transport container and positioned within or in front of the recording apparatus, as a result of which harmful environmental influences can act on the transplant object. The transplant object is usually placed into a sample container for the recordings. A few sample containers in which the recording object is clamped, for example in order to maintain a defined position in the case of a rotational movement of the sample container, are known, for example from DE 10 2016 223 797 A1.

It is therefore an object of the present invention to facilitate improved and reliable analysis and treatment of transplant objects, wherein the transplant object should be dealt with in a particularly sparing and environmental influences-protected manner. Moreover, the information obtained by the analysis should be rendered better usable for medical staff.

The object is achieved by the subjects specified in the main claim and in the alternative independent claims.

Advantageous embodiments are disclosed in the dependent claims, the description and the figures.

Thus, provision is made of a container for receiving a transplant object, said container having a vessel and a closure lid for closing the vessel. By way of example, a container is understood to mean a cup-shaped or tin-shaped receptacle suitable for transporting, treating and storing organic substances or objects. The container is made of at least two parts by virtue of having a vessel and a closure lid that are detachably interconnectable, for example by way of a screw-type connection. In the closed state of the container, the closure lid closes the vessel in liquid-tight, germproof or gas-tight fashion in particular. By way of example, an O-ring may be provided to this end between vessel and closure lid, the closure lid may also have a sealing bead and/or a sealing flank. Increased sterility of the container is facilitated by a germproof or gas-tight closure. For simplified handling, fluting or knurling may be provided on the circumference and/or on the end face of the closure lid such that, for example, it is also possible to grip the container with moisture-loaded gloves. Additionally, a predefined tightness may be provided on a screw-type connection of the vessel with the closure lid such that for example a receiver for a torque wrench can also be arranged on the closure lid. The vessel and/or the closure lid are preferably produced from plastic in order to ensure a low weight, a sufficient sterility, a good passage of radiation, and simple handling. By way of example, polyethylene (PE, HDPE) or polyethylene terephthalate (PET) may be considered as suitable plastics. In particular, the container may also be produced from biocompatible materials.

The container is transmissive to radiation that facilitates radiological image recordings of the transplant object received in the container. Such radiation is understood to mean electromagnetic waves in particular, but also mechanical waves, for example in the ultrasonic range, in the present case. The frequency range of the electromagnetic waves can be in the range of visible light, but for example also in the range of x-ray radiation. In principle, this relates to radiation allowing and/or commonly used for imaging methods in the field of medicine by means of instrument-based optical examination methods, i.e., radiation with which image data of biological structures can be obtained. In particular, the container also facilitates image recordings of the transplant object received in the container implemented by means of magnetic resonance imaging or micro-computed tomography. In this context, micro-computed tomography was found to be particularly suitable as it facilitates very high resolution, distortion-free and overlay-free image recordings of the transplant object. The container preferably has a transparent embodiment in order to be transmissive to radiation in the range of visible light, and consequently in order to also facilitate light-based image recordings of the transplant object. The image recordings are preferably digital image recordings so as to be able to better process these, for example by means of suitable software.

Alternatively or in addition, the container is transmissive to radiation which facilitates a sterilization by means of ionizing radiation of the transplant object received in the container. Sterilization is understood to mean a method, also referred to as sterilizing or degermination, as a result of which the transplant object is freed from viruses and living microorganisms, including their dormancy periods (e.g., spores). In terms of the technical distinction from disinfection, sterilization must bring about the complete removal of all microorganisms with a higher probability. Sterilization using ionizing radiation, also referred to as radiosterilization, can be implemented by means of UV, x-ray or gamma radiation, for example. Irradiation by electrons is also possible.

The closure lid and/or the vessel of the container have one or more affixment structures for fastening the transplant object in the container. Very generally in the context of this application, the words "a/an", unless expressly defined otherwise, should not be understood to be quantifiers but should be understood to be indefinite articles with the meaning of "at least one". Thus, for example, more than one transplant object may also be affixable in the container. If the application refers to a feature on "one or more affixment structures", this can mean individual affixment structures, a plurality of affixment structures or else all available affixment structures on the transplant object. The affixment structures are preferably suitable for interlocking and/or frictional fastening of the transplant object in the container. In this case, the transplant object can be fastened directly, or indirectly via fastening means, to the affixment structure. The affixment structure can be formed in one piece with the vessel and/or the closure lid. The affixment structure may also be present separately and may be mountable on the container when necessary, for example be able to be affixed or adhesively bonded thereto. In this way, the container may also be usable for other purposes and retrofitting of containers with affixment structures for fastening transplant objects is facilitated.

As a result of the radiation-transmissive container it is possible to make radiological image recordings of the transplant object or sterilize the latter by means of ionizing radiation, without having to remove said transplant object from the container. In this way, the transplant object is protected from harmful environmental influences. The affixment structure ensures a defined position of the transplant object in the container. In particular, the transplant object is not simply only placed into the container such that it can be subject to deformations on account of its weight, said deformations not only being able to damage the transplant object but also falsifying radiological image recordings. In particular, this applies to non-dimensionally-stable transplant objects such as heart valves, for example, which collapse in a lying position. As a result of the affixment structure, the contact of the transplant object with the container is reduced to a few defined contact points with the affixment structure, and so the sterility of the object surroundings is increased. By way of example, the affixment structure also facilitates central positioning of the transplant object in the container, and so the radiological image recordings are improved because, for example, no base or lid section of the container covers parts of the transplant object in the images made. As a result of the defined fastening of the transplant object to the affixment structure, an unwanted displacement of said transplant object, for example on account of movements of the container during transport, is moreover prevented.

Consequently, the container facilitates improved and reliable analysis and treatment of transplant objects, wherein the transplant object is dealt with in a particularly sparing and environmental influences-protected manner.

If the closure lid comprises the envisaged affixment structure, the transplant object can be transported in comparatively sparing and low-germ fashion between different vessels and thus, for example, be moved from a pretreatment vessel into a transportation vessel or into a recording vessel for radiological image recordings. In this case, the pretreatment vessel, the transportation vessel and the recording vessel preferably have the same closure structure for the connection to the closure lid, for example the same thread in the case of the screw-type closure. The vessels may optionally have additional features corresponding to their respective purpose, for example the recording vessel may be transparent, the transport vessel may have a cooling device or the pretreatment vessel may have a liquid-tight, germ-proof or gas-tight embodiment. By way of example, the pretreatment may be decellularization, within the scope of which for example a decellularization solution made of an aqueous solution of a strongly anionic detergent is filled into the vessel with the transplant object. To transport or store the transplant object in the container it is in turn conceivable to fill the vessel with a sterile sodium chloride solution or ethanol. By contrast, radiological image recordings are made using a container that is free from liquid or that has a very small amount of liquid in the base region of the vessel for keeping the transplant object moist, so as not to obfuscate the radiological measurement signals.

The invention is particularly suitable for particularly sensitive, light, vulnerable and easily deformable transplant objects. By way of example, this can be a pulmonary valve which represents a rather delicate and sensitive transplant object, having a low mass (often less than 20 grams) and a small size (20-30 millimeters). However, the container is naturally suitable for more stable and larger transplant objects, for example aortic valves.

Sufficient sterility of the utilized medical products should be paid attention to, in particular in the field of transplant medicine. The container according to the invention contributes to this as a result of the improved reception of the transplant object, which container in turn should be classified as a Class IIa medical product pursuant to RL 93/42/EWG and VO 2017/745 on account of the indirect contact with the circulatory system of the living being.

According to an advantageous embodiment, one or more affixment structures are designed for hanging fastening of the transplant object in the container. Consequently, the affixment structure serves to hang up the transplant object by virtue of the transplant object being fastened to one or more mounting points on the affixment structure, either directly or indirectly, for example by means of threads, such that the transplant object floats freely in the container apart from at the mounting points. This realizes particularly few contact points between the transplant object and the container as a result. Moreover, a possible local deformation of the transplant object on account of its fastening to the affixment structure is restricted to the mounting points, while the remainder of the transplant object at least approximately adopts its real physiological form.

According to an advantageous embodiment, one or more affixment structures are in the form of eyelets. By way of example, an eyelet is understood to mean a ring-shaped material loop, although it may also have a rectangular opening contour, for example. The eyelet or the eyelets can be embodied in one piece with the vessel or the closure lid. In particular, the eyelets serve as indirect fastening of the transplant object on the container. By way of example, indirect fastening can be implemented by means of threads, drawstrings or other preferably non-rigid fastening means.

Eyelets represent a comparatively simple, flexible and intuitive fastening option, which is moreover simple to produce. Moreover, the safety of the transplant object is increased if use is made of fastening means such as surgical monofilament or polyfilament suturing material, for example, since the transplant object is only in indirect contact with the container by way of an acknowledged medical product (the surgical suturing material). By way of example, these threads can be sutured to the transplant object or hold the latter by way of simple thread loops. In the case of suturing, the piercing points of the needle can simultaneously be used for bioptate samples, for example for quality testing purposes, in order to keep the injuries to the transplant object as low as possible. At the same time, suturing represents a significantly less invasive fastening option in comparison with clamping solutions, for example.

Alternatively or in addition, however, affixment structures embodied as clamps, clips, hooks or slits or comparable affixment structures suitable for an interlocking and/or frictional connection are also conceivable as a matter of principle.

According to an advantageous embodiment, one or more affixment structures only extend in the spatial volume spanned by the contours of the closure lid. Consequently, the affixment structures do not protrude beyond the plane of the closure lid edge in the direction of the vessel interior but are fully received within the lid structure. This prevents the affixment structures from impairing radiological recordings or a sterilization by means of ionizing radiation, for example by restricting the field of view. The spatial volume spanned by the lid is delimited by the closed lid upper side or end face, the closed lid side face on the circumference of the lid, and the open lid lower side facing the container interior. Consequently, the affixment structure does not intersect a plane spanned by the lower lid edge in this embodiment.

According to an advantageous embodiment, the closure lid has a circular base and one or more affixment structures are arranged concentrically around a center of the circular base. The base is situated on the back side of the end face of the closure lid, that is to say the area identified in the case of an erect container when a closure lid placed on the container is viewed from above. The one or more affixment structures are consequently arranged on the side of the base of the closure lid facing the container interior, that is to say facing the vessel. By way of example, the affixment structure can be formed as a material projection from the base. By way of example, the affixment structure can be arranged at a distance of 10 to 20 mm from the center. A mandrel, to which further accessories are fastenable, can optionally be arranged at the center. The concentric arrangement of the affixment structure around the center of the base promotes central positioning and fastening of the transplant object in the container, and so said transplant object does not come into unwanted contact with the vessel walls, the vessel base or the closure lid edge. Moreover, in particular as a material projection, for instance as an integral constituent part of the closure lid, the affixment structure is easily producible, for example by injection molding or deep drawing.

In this case, the affixment structure can be in the form of a collar formed in one piece with the closure lid in particular, said collar having passage openings in the form of eyelets. A collar is preferably understood to mean a closed, ring-shaped material projection of the closure lid in the direction of the vessel interior when the lid is put on. The collar preferably has a thinner wall than for example the lid side wall on the circumference of the closure lid, in order to facilitate material savings and sufficient leeway, for example within the scope of injection molding. The passage openings are preferably embedded equidistantly in the collar in order to promote an optimal distribution of the weight of the transplant object on the closure lid. Moreover, this embodiment of the container is simple to produce and easy to equip.

According to an advantageous embodiment, the transplant object is affixable in the container by way of a three-point mount using the one or more affixment structures. Consequently, for example a three-part affixment structure is present or three affixment structures, for example three eyelets, are present. As a result, three contact points are also provided on the transplant object, for example three suturing points. The contact points are connected to the affixment structure of the container by means of fastening means, for example threads. The three contact points are preferably chosen in relation to the center of mass of the transplant object in such a way that the latter hangs freely in the container without coming into contact with a vessel wall or comparable structure of the container. In this case, three contact points represent the ideal compromise between as little injury to the transplant object as possible and a stable mount. The three-point meant was found to be equally suitable for stable and heavy transplant objects, for example aortic valves, and for sensitive, light objects such as a pulmonary valves, for example.

According to an advantageous embodiment, the vessel can have a substantially cuboid form and/or can have an optical graduation on at least one side edge.

On account of the plane side walls, the cuboid form simplifies taking image recordings in the visible and short-wavelength range (x-ray, gamma radiation), without having a negative effect on the passing radiation as a result of curvature of the vessel wall or possibly without producing optical side effects. A distortion-free optical inspection is facilitated by way of comparatively large, plane side areas. If the vessel has side edges, as is conceivable in the case of a cuboid form for example, a scale or graduation arranged on the side edges may simplify the defined filling of liquids, for example for the pretreatment. At the same time, the graduation is not on the optical axis during the image recordings such that the examined transplant object is not concealed by a print or imprint.

However, it is naturally also conceivable as a matter of principle to envisage round vessels without edges for the container. Particularly in the case of x-ray- or resonance-based radiological methods, including micro-computed tomography, there is a sufficient radiation transmissivity in the case of preferably plastics-based containers such that the shape or a print or imprint on the container is negligible.

The object of the invention is also achieved by a closure lid or a vessel having one or more affixment structures in accordance with the above-described features. The advantages according to the invention are also obtained therewith.

Further, the invention relates to a method for providing three-dimensional structure data of a transplant object. Such three-dimensional structure data are understood to mean all data forms suitable for reproducing the structure of an object. In particular, this relates to the three-dimensional shape, nature, surfaces and generally the morphological structure of the object. By way of example, the three-dimensional structure data may be in the form of a point cloud or dot cloud, and consequently may be available as spatial coordinates of a vector space. Moreover, the three-dimensional data may be converted into graphical representations or CAD data, for example.

The method includes the following steps:
a) fastening the transplant object to an affixment structure of a container transmissive to radiological radiation, in particular a container in accordance with the above-described features;
b) positioning the container in an apparatus for radiological imaging;
c) carrying out the radiological imaging of the transplant object with the aid of the apparatus;

d) converting the imaging results into three-dimensional structure data of the transplant object with the aid of an evaluation unit;

e) providing the structure data of the transplant object in a database.

Thus, image recordings of the transplant object are initially created with the aid of a container transmissive to radiological radiation, said container having an affixment structure and being placed in a radiology apparatus such as a micro-computed tomography apparatus or an MRI apparatus, for example. In this case, too, radiological imaging is understood to mean optical examination methods based on electromagnetic waves or mechanical waves. The image data obtained are converted into three-dimensional structure data, to be precise by means of an evaluation unit that is in the form of a computer for example. To this end, the evaluation unit comprises suitable hardware and/or software to convert the measured reflection radiation, nuclear magnetic resonances or similar analysis criteria into image data and three-dimensional data such as coordinates of a vector space for example. The data are subsequently stored in a database such that they are uniquely assigned to the analyzed transplant object, which is identifiable by way of an ID, for example, in the database. The database may be a database system of the actual database and a database management system. By way of example, the database may be a relational database with a tabular structure. The database may contain at least an ID and the structure data of the transplant object linked therewith. The database may also contain further data linked to the transplant object, for example origin data, age and various categorizations. For instance, the provision of the structure data can be implemented by way of a download option via an internal or external, more particularly authorized access to the database, for example via an internal or public network.

The provided three-dimensional structure data are utilizable in multifaceted ways and are conveniently usable for medical staff, in particular for example by exploiting complementary analysis software, for example for quality control or for verifying the transplant receivers for whom the present transplant object is suitable on account of its determined properties. Consequently, the information obtained by the analysis is rendered better usable for medical staff. In this context, the three-dimensional structure data are substantially more accurate than text descriptions and photographs of the transplant object, as were conventional until now. In particular, small individuality properties and peculiarities, for example calcifications and fenestrations, which may be highly relevant to the success of the transplant, can be detected more precisely. Additionally, an exact measurement of the transplant object is facilitated, and so the provided data are available as biometric information. The data accuracy can be increased, in particular by way of high-resolution radiological methods such as micro-computed tomography, and the analysis results can consequently be refined.

According to an advantageous embodiment, there can be a pretreatment of the transplant object in a separate pretreatment container or in the container of step a) in a step z) of the method which precedes step a). To this end, the pretreatment container may have an affixment structure, in particular an affixment structure in accordance with the above-described features, or may have an embodiment comparable to the container in accordance with the above-described features. By way of example, the pretreatment may be decellularization, within the scope of which for example a decellularization solution made of an aqueous solution of a strongly anionic detergent is filled into the vessel with the transplant object.

According to an advantageous embodiment, the conversion of the imaging results into three-dimensional structure data of the transplant object may contain a computational correction of possible deformations of the transplant object that may occur on account of it being fastened in the container. In this case, deformations in the region of the fastening are determined by calculation, for example on the basis of the mass and weight of the transplant object, its center of mass and the position of the fastening points, for example mounting points, and correction values are applied to the obtained three-dimensional structure data, for example by subtraction. The calculation can also be implemented on the basis of simulation models and, in particular, be assisted by suitable simulation software. The correction by calculation facilitates a model refinement of the three-dimensional model of the transplant object, and so realistic structure data, which are very close to the actual physiological form of the transplant object, are producible.

According to an advantageous embodiment, the conversion of the imaging results into three-dimensional structure data of the transplant object may contain a background subtraction, a frame edge extraction, 360° frame combination, manual contour post processing and/or a point cloud conversion. In this way, further advantageous image post processing for improving the analysis result and for providing even more precise structure data is included in the preparation. During the image processing, the image information from individual recordings ("scans") are in particular fused and reconstructed together to form a three-dimensional image. Particularly in the case of heart valves as transplant objects, radiological image recordings are low contrast, and so subsequent automatic or manual image processing is advantageous. In this context, it is also possible to use AI-based image processing software with machine learning capability in order to increasingly automate the image processing by way of training data records or repeating patterns.

According to an advantageous embodiment, the conversion of the imaging results into three-dimensional structure data of the transplant object may contain the generation of virtual sectional images. Virtual sectional images are very helpful, in particular for the further quality control and suitability test of the transplant object, and are of great use to the medical staff since it is also possible to determine, e.g., diameter and wall thickness of the transplant object or of individual parts thereof in a substantially simpler and more accurate manner. Radiological imaging by means of micro-computed tomography is particularly suitable for the generation of virtual sectional images since distortion-free, superposition-free sectional images with a very high detail resolution are able to be created therewith.

According to an advantageous embodiment, the structure data in step e) can be provided in a format suitable for import into surgery planning programs. By way of example, U3D ("Universal 3D") is a standardized format which is used in conventional programs for surgery planning. If the three-dimensional structure data of the transplant object are converted into such a format, the compatibility of the data with programs for further processing in the field of surgery planning is increased. Consequently, the data are directly usable for the medical staff in particular without additional conversion outlay or data losses, and can be directly included in the transplant preparation.

The object of the invention is also achieved by a system for providing three-dimensional structure data of a transplant object, wherein the system comprises a container having one or more affixment structures for fastening the transplant object, in particular a container in accordance with the above-described features, an apparatus for radiological imaging of the transplant object fastened in the container, an evaluation unit for converting the imaging results into three-dimensional structure data of the transplant object, and a database for providing the three-dimensional structure data. The advantages according to the invention are also obtained therewith.

The object of the invention is also achieved by a method for sterilizing a transplant object by means of ionizing radiation. The method includes the following steps:
  a) fastening the transplant object to an affixment structure of a container, in particular a container in accordance with the above-described features;
  b) positioning the container in a sterilization apparatus;
  c) carrying out the sterilization of the transplant object by means of ionizing radiation using the sterilization apparatus.

The advantages according to the invention are also obtained therewith. In this case, the sterilization apparatus can be designed to receive a container with a transplant object, for example in a sterilization chamber, and to produce ionizing radiation, for example as UV, x-ray, gamma and/or electron radiation, and to direct said ionizing radiation at the container with the transplant object.

The object of the invention is also achieved by a system for sterilizing a transplant object by means of ionizing radiation, wherein the system comprises a container having one or more affixment structures for fastening the transplant object, in particular a container in accordance with the above-described features, and an apparatus for sterilization by means of ionizing radiation. The advantages according to the invention are also obtained therewith. In this case, the sterilization apparatus can be designed to receive a container with the transplant object, for example in a sterilization chamber, and to produce ionizing radiation, for example as UV, x-ray, gamma and/or electron radiation, and to direct said ionizing radiation at the container with the transplant object.

The invention will be explained in more detail below on the basis of an exemplary embodiment using the attached drawings, in which schematically:

Figure 1:
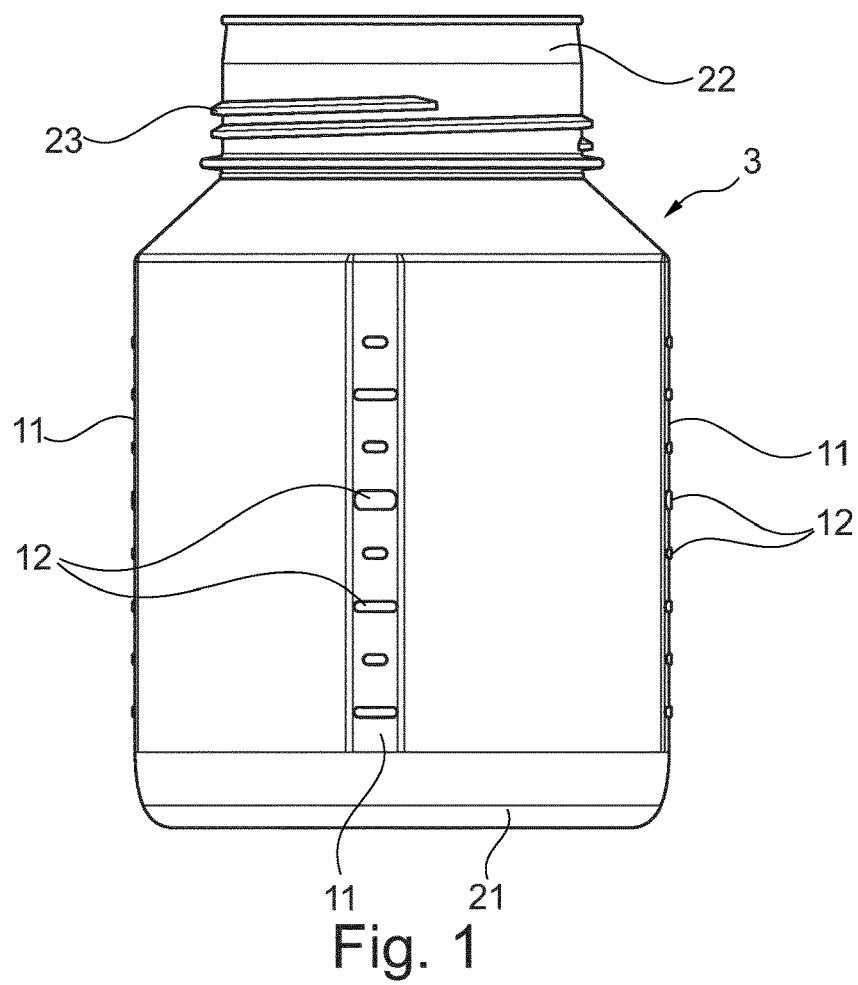
FIG. 1 shows a vessel of a container for receiving a transplant object.
Figure 3:
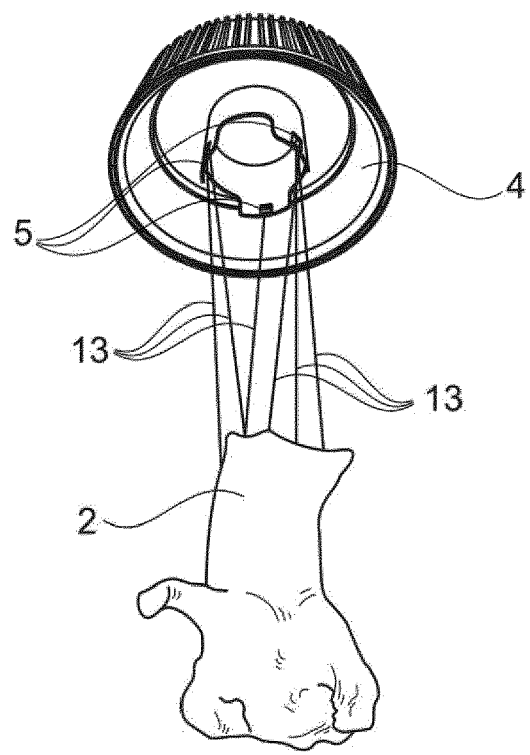
FIG. 3 shows the closure lid with a transplant object fastened thereto.
Figure 4:
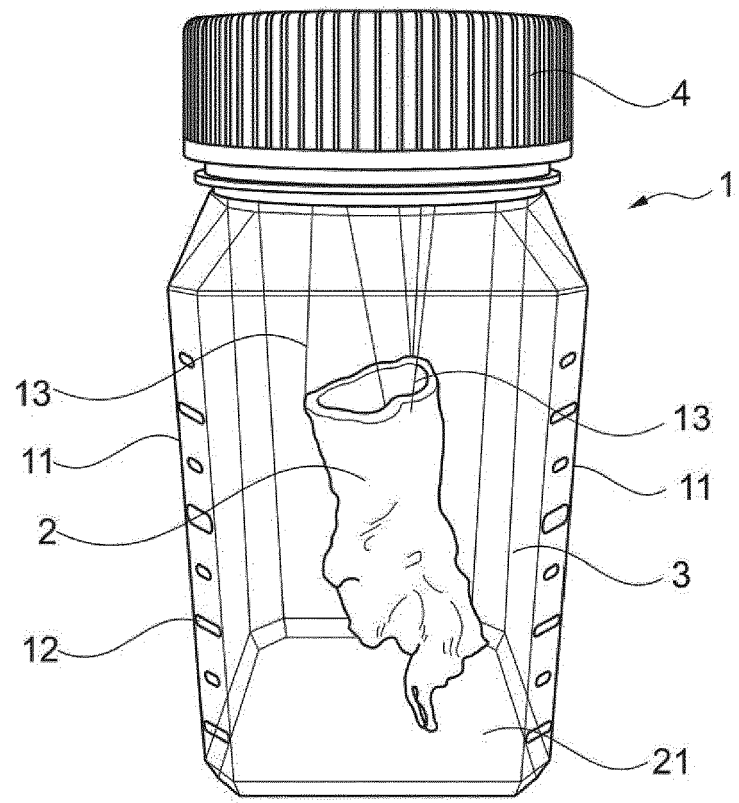
FIG. 4 shows the container with vessel, closure lid and transplant object.

FIG. 1 shows a side view of a vessel 3 of a container 1, shown inter alia in FIG. 4, for receiving a transplant object 2, shown inter alia in FIG. 3. The vessel 3 is transmissive to radiation which facilitates radiological image recordings and/or a sterilization by means of ionizing radiation of the transplant object 2 received in the container 1. The vessel 3 preferably has a transparent embodiment in order to additionally be transmissive to radiation in the range of visible light. In that exemplary embodiment shown, the vessel 3 has a cuboid basic shape with side edges 11, on which there is an optical graduation 12. The graduation 12 can simplify the defined filling of liquids, for example for the pretreatment, or assist an object measurement in image recordings of the container 1 with the transplant object 2.

The vessel 3 has a rectangular vessel base 21 and a vessel neck 22 which is opposite to the vessel base 21 and, deviating from the basic shape of the vessel 3, has a round, in particular circular cross section. The vessel neck 22 has a screw thread 23 that can be made to engage with a corresponding screw thread 24 of a closure lid 4, the latter shown in FIG. 2, in order to establish a detachable connection between the vessel 3 and the closure lid 4 and in order consequently to close the vessel 3 using the closure lid 4 when necessary. Together, the vessel 3 and the closure lid 4 form the container 1 for receiving a transplant object 2. In the closed state of the container 1, the closure lid 4 closes the vessel 3 in liquid-tight, germproof or gas-tight fashion in particular. To this end, provision can for example optionally also be made of an O-ring, not shown here, a sealing bead or a sealing flank on the closure lid 4 or the vessel 3.

The vessel 3 can be a pretreatment vessel, a transportation vessel and/or a receiving vessel for the transplant object 2. By way of example, the vessel 3 may have been produced by means of injection stretch blow molding.

Figure 2:
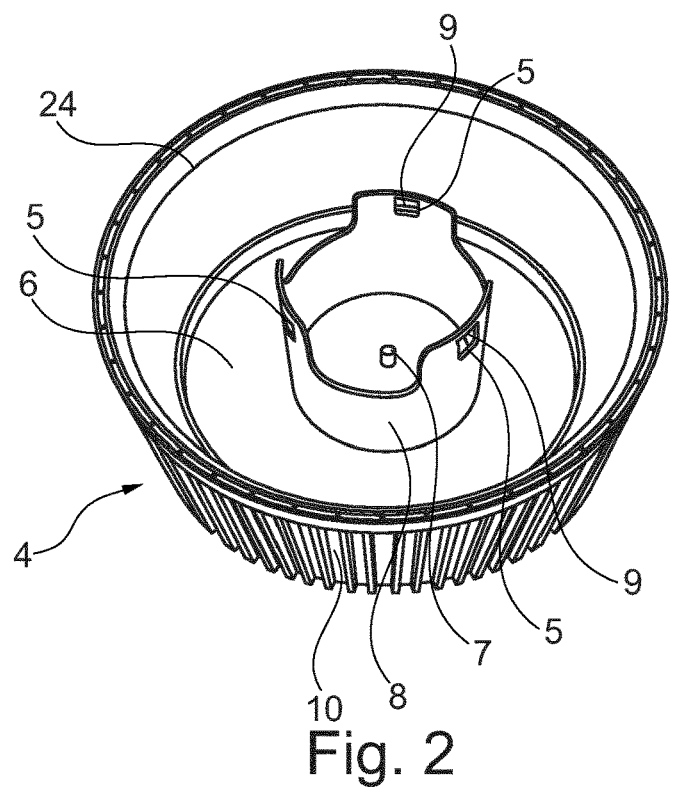
FIG. 2 shows a closure lid of the container for closing the vessel.

FIG. 2 shows a perspective view of a closure lid 4 of the container 1, which is able to be screwed onto the vessel 3, shown in FIG. 1, by means of a screw thread 24. By way of example, the closure lid 4 can be an injection molded part. On the circumference, the closure lid 4 has fluting 10 formed by external ribs in order to simplify the handling of the closure lid 4, especially with gloves as well.

The closure lid 4 comprises a plurality of affixment structures 5, which are formed in one piece with the closure lid 4 and which serve to fasten the transplant object 2 in the container 1. In the exemplary embodiment shown, the affixment structures 5 are in the form of eyelets in order to facilitate hanging fastening of the transplant object 2, for example by means of threads 13 shown in FIG. 3. In this case, the threads 13 may firstly be sutured to the transplant object 2, or loosely engage around the latter, and secondly be guided through the eyelets of the closure lid 4 or be secured to the latter in a knot, in order to fasten the transplant object 2 on the closure lid 4 in hanging fashion. Other affixment structures are naturally also conceivable, for example clamp or hook structures shaped onto the closure lid 4, in order to be able to dispense with additional connecting means such as threads 13. However, additional connection means, for example the threads 13 shown, facilitate an individual and flexible spacing of the transplant object 2 from the closure lid 4. Moreover, the threads 13 bring about tissue-sparing fastening of the transplant object 2 on the closure lid 4.

According to the embodiment shown in FIG. 2, the closure lid 4 has a circular base 6 and three affixment structures 5 are arranged concentrically around a center 7 of the circular base 6. This realizes a three-point mount, which facilitates a stable mount of the transplant object 2 while minimizing object injuries. In this case, the affixment structures 5 are in the form of a collar 8 formed in one piece with the closure lid, said collar having passage openings 9 in the form of eyelets. The passage openings 9 are embedded equidistantly in the collar 8 in order to promote an optimal distribution of the weight of the transplant object 2 on the closure lid 4. A mandrel, to which further accessories are fastenable, can moreover be arranged at the center 7.

All constituent parts of the closure lid 4 shown in FIG. 2 are formed in one part with the closure lid 4. However, it is also conceivable that components such as the affixment structures 5, for example, are produced separately and subsequently detachably or non-detachably connected to the closure lid 4, for example in interlocking or frictional fashion. This can facilitate a retrofitability of existing closure lids or a needs-based convertibility of a container 1.

FIG. 3 shows a perspective view of a closure lid 4 with a transplant object 2 that is fastened by way of threads 13 to the affixment structures 5 of the closure lid 4. As is evident, the transplant object 2 can be transported comparatively easily and with comparatively little contamination into the vessel 3 as a result of being fastened to the closure lid 4.

FIG. 4 shows a perspective view of the container 1 composed of the vessel 3 and the closure lid 4, together with a transplant object 2 fastened to the container 1. The closure lid 4 is screwed onto the vessel 3 and closes the latter preferably in sealing fashion. It is evident that the transplant object 2 is fastened to the closure lid 4 by means of threads 13 and hangs freely in the container 1, that is to say without direct contact with the vessel wall or the closure lid 4. The fastening of the transplant object 2 in the container 1 being restricted to a few contact points not only reduces the risk of contamination of the transplant object 2 but also leads to the latter adopting a largely natural, approximately distortion-free state such that image recordings of the transplant object 2 taken in this state are able to reproduce the actual structure of the transplant object 2 virtually without distortions.

Figure 5:
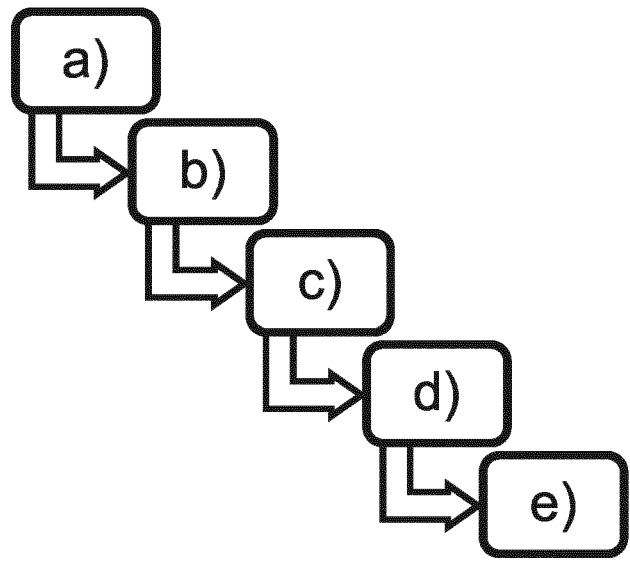
FIG. 5 shows a method for providing three-dimensional structure data of a transplant object.

FIG. 5 shows a method for providing three-dimensional structure data of a transplant object 2. In a first method step a) the transplant object 2 is fastened to an affixment structure 5 of a container 1, in particular a container 1 in accordance with the above-described features. By way of example, fastening can be mounting, clamping or hooking the transplant object 2 on the closure lid 4 or the vessel 3. In a second method step b) that follows the first method step a), the container 1 is positioned in an apparatus 15 for radiological imaging, for example shown in FIG. 7. By way of example, the apparatus 15 can be a micro-computed tomography apparatus. Between fastening and positioning, the transplant object 2 may have to be transported to the apparatus 15. By way of example, positioning may be a placement and/or an affixment of the container 1 in a receiving chamber of the apparatus 15, wherein the receiving chamber for example may have a holding structure, in which the container 1 is positionable and affixable. In a third method step c) that follows the second method step b), the radiological imaging of the transplant object 2 is carried out with the aid of the apparatus 15. In the process, the transplant object 2 is exposed to a specified radiation through the radiation-transmissive container 1, the reflections or resonances of which or other interaction effects of the transplant object 2 with the radiation being detected by the apparatus 15 and being recorded as imaging results. In a method step d) that follows the third method step c) or occurs simultaneously therewith, the imaging results are converted into three-dimensional structure data of the transplant object 2 with the aid of an evaluation unit, for example the evaluation unit 16 shown in FIG. 7. By way of example, the evaluation unit 16 can be a PC, a workstation, a laptop or an external server that is reachable via a given network. The evaluation unit 16 has a suitable data processing software, in particular image processing and image evaluation programs, which are able to further process the imaging results of the apparatus 15. Three-dimensional structure data are understood to mean all data forms suitable for reproducing the structure of an object. In particular, this relates to the three-dimensional shape, nature, surfaces and generally the morphological structure of the object. By way of example, the three-dimensional structure data may be in the form of a point cloud or dot cloud, and consequently may be available as spatial coordinates of a vector space. Moreover, the three-dimensional data may be converted into graphical representations or CAD data, for example. In a method step e) that follows the fourth method step d) or runs at the same time, the structure data of the transplant object 2 are provided in a database 17, for example as shown in FIG. 8. The database 17 may be a database system of the actual database and a database management system. By way of example, the database 17 may be a relational database with a tabular structure. The database 17 may contain at least an ID and the structure data of the transplant object 2 linked therewith. The database 17 may also contain further data linked to the transplant object 2, for example origin data, age and various categorizations. For instance, the provision of the structure data can be implemented by way of a download option via an internal or external, more particularly authorized access to the database 17, for example via an internal or public network.

Figure 6:
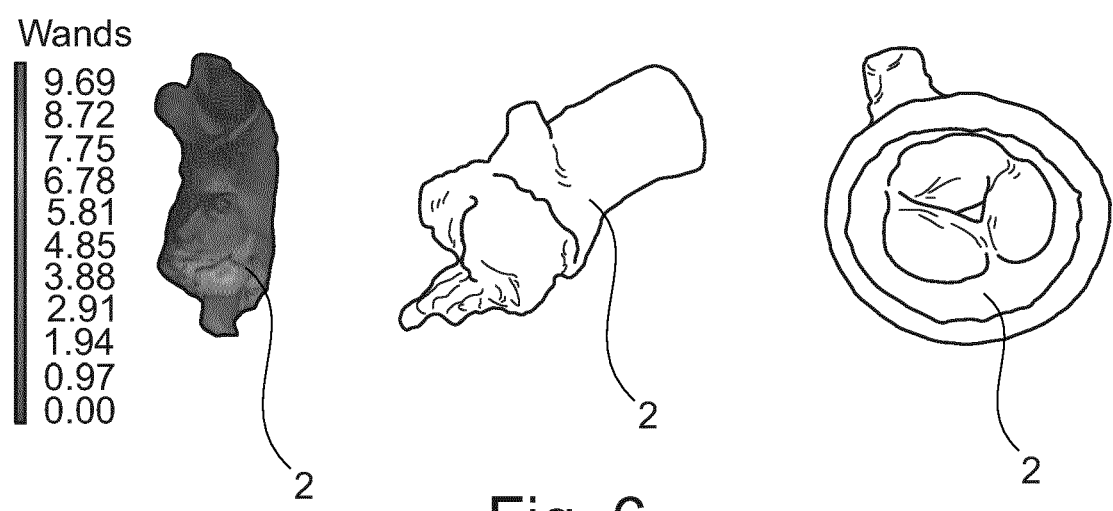
FIG. 6 shows virtual representations of a transplant object.

FIG. 6 shows virtual representations of a transplant object 2, which are producible from the three-dimensional structure data of the transplant object 2. Consequently, for example differently colored or differently shaded 3-D models of the transplant object 2 can be visualized as a virtual representation (left image in FIG. 6), with the color or shading intensity being able to differentiate between different wall thicknesses. Additionally, a realistic 3-D image representation of the transplantation object 2 can be reproduced as a virtual representation (central image in FIG. 6). Virtual sectional images, as may be gathered for example from the image to the right in FIG. 6, are of particular interest in relation to technical and medical analyses of the transplant object 2. In these sectional images, structural details such as the wall thickness profile, for example, can be exactly imaged, and assessed, in a certain plane.

Figure 7:
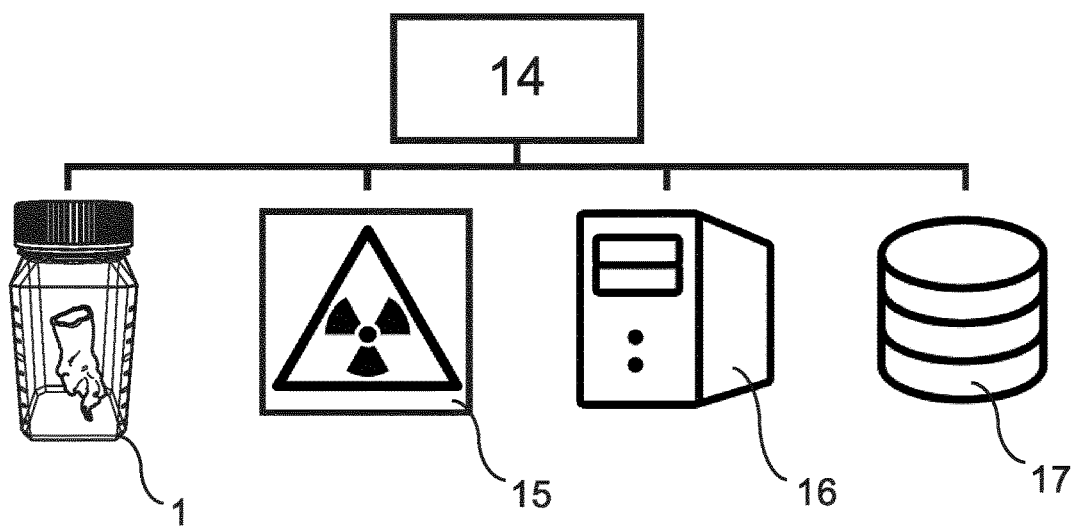
FIG. 7 shows a system for providing three-dimensional structure data of a transplant object.
Figure 8:
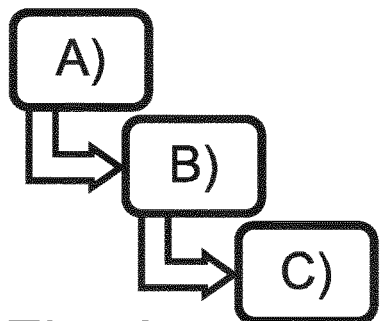
FIG. 8 shows a method for sterilizing a transplant object by means of ionizing radiation.

FIG. 7 shows a system 14 for providing three-dimensional structure data of a transplant object 2. The system 14 comprises a container 1 having one or more affixment structures for fastening the transplant object 2. Moreover, the system 14 comprises an apparatus 15 for radiological imaging, for example a micro-computed tomography apparatus. The system 14 furthermore comprises an evaluation unit 16 for converting the imaging results into three-dimensional structure data of the transplant object 2. By way of example, the evaluation unit 16 can be a PC, a workstation, a laptop or an external server that is reachable via a given network. The evaluation unit 16 has a suitable data processing software, in particular image processing and image evaluation programs, which are able to further process the imaging results of the apparatus 15. The system 14 moreover comprises a database 16 for providing the three-dimensional structure data.

FIG. 8 shows a method for sterilizing a transplant object 2 by means of ionizing radiation. By way of example, the ionizing radiation can be UV, x-ray, gamma or electron radiation. In a first method step A) the transplant object 2 is fastened to an affixment structure 5 of a container 1, in particular a container 1 in accordance with the above-described features. By way of example, fastening can be mounting, clamping or hooking the transplant object 2 on the closure lid 4 or the vessel 3. In a second method step B) that follows the first method step A), the container 1 is positioned in a sterilization apparatus 19, for example shown in FIG. 9. The sterilization apparatus 19 is configured to produce ionizing radiation and may be an x-ray sterilization apparatus, for example. Between fastening and positioning, the transplant object 2 may have to be transported to the sterilization apparatus 19. By way of example, positioning may be a placement and/or an affixment of the container 1 in a receiving chamber of the sterilization apparatus 19, wherein the receiving chamber for example may have a holding structure, in which the container 1 is positionable and affixable. In a third method step C) that follows the second method step B), the sterilization of the transplant object 2 is carried out by means of ionizing radiation using the sterilization apparatus. In the process, the transplant object 2 is exposed to a given radiation through the radiation-transmissive container 1, said radiation freeing the transplant object 2 and/or the container 1 from unwanted microorganisms and consequently establishing sterility of the transplant object 2 and/or of the container 1.

Figure 9:
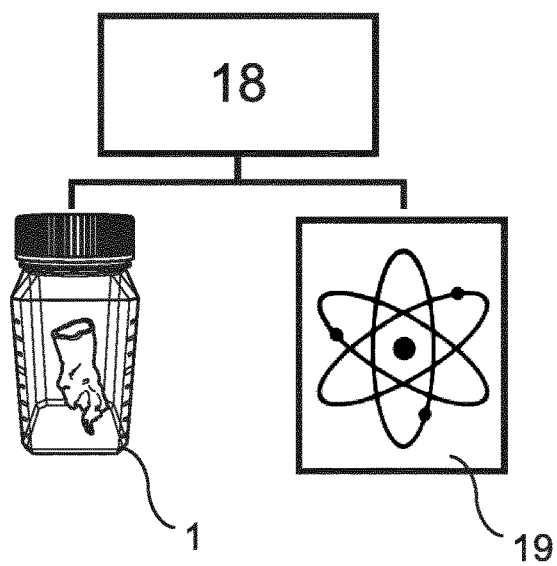
FIG. 9 shows a system for sterilizing a transplant object by means of ionizing radiation.

FIG. 9 shows a system 18 for sterilizing a transplant object 2 by means of ionizing radiation. The system 18 comprises a container 1 having one or more affixment structures 5 for fastening the transplant object 2, in particular a container 1 in accordance with the above-described features, and a sterilization apparatus 19 for sterilization by means of ionizing radiation.

LIST OF REFERENCE SIGNS

1 Container
2 Transplant object
3 Vessel
4 Closure lid
5 Affixment structure
6 Base
7 Center
8 Collar
9 Passage openings
10 Fluting
11 Side edge
12 Graduation
13 Thread
14 System for radiological imaging
15 Apparatus for radiological imaging
16 Evaluation unit
17 Database
18 System for sterilization
19 Sterilization apparatus
21 Vessel base
22 Vessel neck
23 Screw thread on vessel
24 Screw thread on lid
a) Fasten
b) Position
c) Implement
d) Convert
e) Provide
A) Fasten
B) Position
C) Implement

The invention claimed is:

1. A container for receiving a transplant object, comprising:
a vessel; and
a closure lid for closing the vessel,
wherein the container is sufficiently transmissive to radiation so as to facilitate radiological image recordings and/or a sterilization by ionizing radiation of the transplant object when in the container, and
wherein the closure lid and/or the vessel have one or more affixment structures for fastening the transplant object in the container.

2. The container as claimed in claim 1, wherein the one or more affixment structures are designed for fastening of the transplant object in the container in a hanging orientation.

3. The container as claimed in claim 1 wherein each of the one or more affixment structures is in a form of an eyelet.

4. The container as claimed in claim 1 wherein each of the one or more affixment structures only extend in a spatial volume spanned by contours of the closure lid.

5. The container as claimed in claim 1 wherein the closure lid has a circular base, and wherein the one or more affixment structures are arranged concentrically around a center of the circular base.

6. The container as claimed in claim 5, wherein at least one affixment structure of the one or more affixment structures is in a form of a collar formed in one piece with the closure lid, said collar having passage openings in a form of eyelets.

7. The container as claimed in claim 1 wherein at least one of the one or more affixment structures is configured as part of or to interact with a three point mount to which the transplant object is mountable.

8. The container as claimed claim 1 wherein the vessel has a substantially cuboid form and/or has side edges and an optical graduation on at least one side edge.

9. A closure lid having one or more affixment structures for a container as claimed in claim 1.

10. A vessel having one or more affixment structures for a container as claimed in claim 1.

11. A method for providing three-dimensional structure data of a transplant object, comprising:
a) fastening the transplant object to an affixment structure of a container as claimed in claim 1;
b) positioning the container in an apparatus for radiological imaging;
c) carrying out radiological imaging of the transplant object using the apparatus;
d) converting imaging results into three-dimensional structure data of the transplant object using an evaluation unit;
e) providing the three-dimensional structure data of the transplant object in a database.

12. The method as claimed in claim 11, wherein the converting of the imaging results into three-dimensional structure data of the transplant object comprises a computational correction of possible deformations of the transplant object that may occur on account of the transplant object it being fastened in the container.

13. The method as claimed in claim 11 wherein the converting of the imaging results into three-dimensional structure data of the transplant object comprises generating virtual sectional images.

14. The method as claimed in claim 11 wherein the three-dimensional structure data is providable from the database in a format suitable for import into surgery planning programs.

15. A method for sterilizing a transplant object by ionizing radiation, comprising:
A) fastening the transplant object to an affixment structure of a container, as claimed in claim 1;
B) positioning the container in a sterilization apparatus;

C) carrying out sterilization of the transplant object by ionizing radiation using the sterilization apparatus.

16. A system for sterilizing a transplant object by ionizing radiation, comprising:
- a container having one or more affixment structures for fastening the transplant object, wherein the container is as claimed in claim 1, and
- a sterilization apparatus for sterilization by ionizing radiation.

17. A system for providing three-dimensional structure data of a transplant object, comprising:
- a container having one or more affixment structures for fastening the transplant object,
  - an apparatus for radiological imaging of the transplant object fastened in the container,
  - an evaluation unit for converting imaging results into three-dimensional structure data of the transplant object, and
  - a database for providing the three-dimensional structure data.

18. The system of claim 17 wherein the container is as is claimed in claim 1.

* * * * *